United States Patent [19]

Kawagishi et al.

[11] Patent Number: 5,391,544
[45] Date of Patent: Feb. 21, 1995

[54] CYATHANE DERIVATIVES AND ANTIMICROBIAL AGENTS CONTAINING SAME

[75] Inventors: Hirokazu Kawagishi, Shizuoka; Fumihiro Ojima, Tochigi; Kenji Okamoto, Tochigi; Hideki Sakamoto, Tochigi; Yukio Ishiguro, Tochigi, all of Japan

[73] Assignee: Kagome Kabushiki Kaisha, Aichi, Japan

[21] Appl. No.: 196,049

[22] Filed: Feb. 10, 1994

[51] Int. Cl.$^6$ .................. A61K 31/70; A61K 31/335; C07H 15/24; C07D 321/00
[52] U.S. Cl. ........................... 514/33; 514/451; 514/452; 514/453; 536/1.11; 536/4.1; 536/7.1; 536/16.8; 549/357; 549/358; 549/377; 549/382
[58] Field of Search .................... 536/16.8, 7.1, 1.11, 536/4.1; 549/358, 357, 377, 382; 514/33, 452, 453, 451

[56] References Cited

PUBLICATIONS

Ayer et al, "Terpenoid Metabolites of Mushrooms and Related Basidiomycetes", Tetrahedron 37:2199–2248 (1981).

Okamoto et al, "Antimicrobial Chlorinated Orcinol Derivatives From Mycelia of *Hericium erinaceum*," Phytochemistry 34(5):1445–46 (1993).

Kawagishi et al, "Eninacines A, B and C, strong stimulators of nerve growth factor synthesis, from the mycelia of *Hericuum erinaceum*," Tetrahedron Letters, 35(10):1569–1572 (1994).

*Primary Examiner*—Douglas W. Robinson
*Assistant Examiner*—Francisco C. Prats
*Attorney, Agent, or Firm*—Heller, Ehrman, White & McAuliffe

[57] ABSTRACT

New cyathane derivatives shown by Formula (1) or (2) given below have the effect of stimulating production of nerve growth factors and antimicrobial effects:

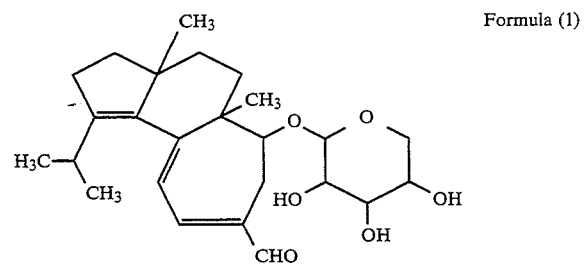

Formula (1)

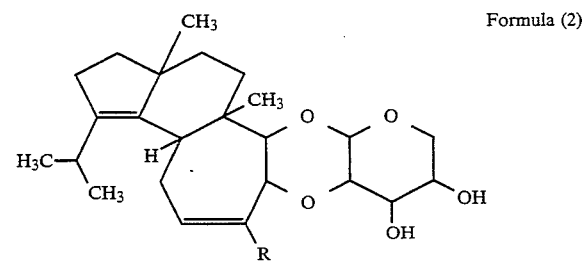

Formula (2)

where R is either CHO or CH$_2$OH.

4 Claims, No Drawings

CYATHANE DERIVATIVES AND ANTIMICROBIAL AGENTS CONTAINING SAME

BACKGROUND OF THE INVENTION

This invention relates to cyathane derivatives isolated from culture mycelia of Hericium erinaceum which is a mushroom of the Hydnaceae family in the Hericium group. This invention further relates to production stimulators of nerve growth factors (hereinafter referred to as NGF) and antibacterial agents containing such cyathane derivatives.

There have been reports on compounds isolated from mushrooms as well as their pharmacological effects. For example, it has been reported in Tetrahedron 39, 2779–2785 (1983) that ergosterol derivatives isolated from Polyporus versicolor, which is a mushroom in the Polyporaceae family, have the effect of killing hepatoma cells. As another example, it has been reported in Phytochemistry 27, 2777–2789 (1988) that erogosterol derivatives isolated from Agaricus blazei, which is a mushroom in the Agaricaceae family, have the effect of killing hela cells. Similar effects have been reported also in Japanese Patent Publications Tokko 48-6766, 55-71702 and 58-62118.

Regarding Hericium erinaceum which is a mushroom in the Hydnaceae family, it has been reported in Japanese Patent Publications Tokkai 3-157347, 3-157367 and 3-157379 that octadecenoic acid derivatives, isoindolinone derivatives and phthalide derivatives separated from this mushroom have the effects of killing hela cells. There have not been reports, however, on compounds isolated from culture mycelia of Hericium erinaceum.

SUMMARY OF THE INVENTION

It is therefore an object of the present invention to ascertain pharmacological effects of the compounds isolated from culture mycelia of Hericium erinaceum.

Another object of the invention is to provide production stimulators of nerve growth factors and antimicrobial agents containing such compounds.

The present invention is based on the discovery made as a result of diligent studies by the present inventors on compounds isolated from culture mycelia of Hericium erinaceum, as well as their pharmacological effects, that new cyathane derivatives can be isolated by applying specified extraction and division processes on culture mycelia of Hericium erinaceum and that such cyathane derivatives have the effect of stimulating production of nerve growth factors as well as antimicrobial effects.

DETAILED DESCRIPTION OF THE INVENTION

This invention relates to cyathane derivatives shown by Formulas (1) and (2) shown below, as well as production stimulators of NGF and antimicrobial agents containing such cyathane derivatives as their effective component:

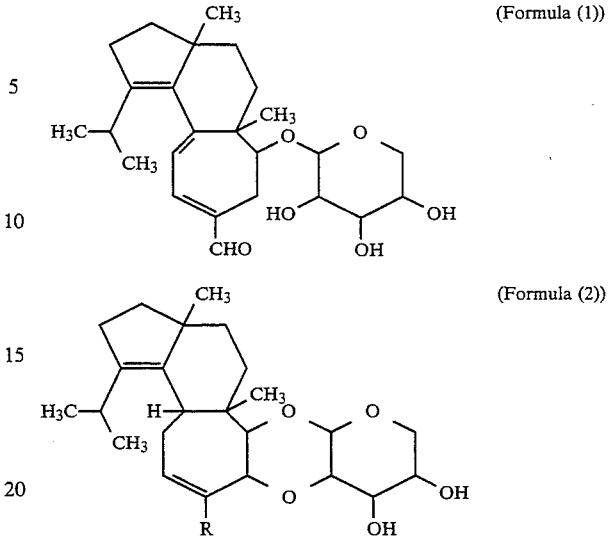

where R is either CHO or $CH_2OH$. Cyathane derivatives shown by Formulas (1) and (2) can be isolated from mycelia of Hericium erinaceum as follows. First, mycelia of Hericium erinaceum are cultured for four weeks at 30° C. in a SGC medium (which is a liquid medium comprising glucose, starch, corn steep liquor, $KH_2PO_4$, $CuSO_4$, $ZnCl_2$, thiamine chloride and water, adjusted to pH=5.3–5.5).

After the culture is separated by centrifugal separation into a supernatant and a precipitate containing culture mycelia, the culture mycelia are extracted by a uniformly mixed solvent of water and a water-soluble organic solvent. Examples of such uniformly mixed solvent for this purpose include 80–85% aqueous solution of methanol or ethanol and 85% aqueous solution of acetone. Extraction is normally carried out at room temperature but may also be carried out by a reflux method with heating. The time required for the extraction is normally 1–72 hours. For example, a water phase can be obtained by adding cultured mycelia of Hericium erinaceum into an 85% ethanol aqueous solution of ethanol, homogenizing it, leaving it for a day and a night at room temperature, thereafter obtaining a liquid extract by filtration, and evaporating the ethanol by heating this liquid extract under a reduced pressure condition at 40°–45° C.

Next, this water phase is subjected to a liquid-liquid partition extraction process by using water and a water-insoluble organic solvent to separate a water-insoluble organic solvent layer, and a dried solid object is obtained by evaporating the water-insoluble organic solvent from this water-insoluble organic solvent layer. Examples of water-insoluble organic solvent to be used for this purpose include chloroform, ethyl acetate and diethylether. Such a dried solid object may be obtained, for example, by adding ethyl acetate to such a water phase, shaking it and then leaving it quietly to thereby separate a layer of ethyl acetate, and causing ethyl acetate to evaporate by heating this ethyl acetate layer by heating at 40°–45° C. under a reduced pressure condition.

The dried solid object, thus obtained, is itself effective as a production stimulator of NGF and an antimicrobial agent, but cyathane derivatives of the present invention may be isolated therefrom, in order to improve the effect of stimulating the production of NGF as well as the antimicrobial effect by removing impurities therefrom, subjecting this object to a chromatographical separation process and further separating the once chromatographically separated sample. As will be explained below more in detail, the chromatographical separation process can be silicagel column chromatography or thin-layer chromatography using mobile phases with different polarities comprising, for example, a chloroform-acetone combination or a hexane-ether combination. As another example, the second separation process may be effected by high performance liquid chromatography using an ODS column.

As will also be explained below further in detail, three kinds of compound are separated after the second separation process Analyses show that a first of these three kinds has the following physical and chemical properties and the structure:

(1) Molecular-weight: 432 ($C_{25}H_{36}O_6$)
(2) infrared spectrum: 3420, 1675, 1654, 1577 $cm^{-1}$
(3) Chemical shift by $_1$H-NMR: $\delta$0.91 (3H, d, J=6.60), 0.93 (6H, s), 0.98 (3H, d, J=6.60), 1.30 (1H, d, J=13.21), 1.63 (2H, m), 1.68 (2H, m), 2.12 (1H, m), 2.35 (2H, m), 2.48 (1H, d, J=17.60), 2.77 (1H, heptet, J=6.60), 3.20 (1H, dd, J=11.74, 6.96), 3.24 (1H, dd, J=17.60, 5.87), 3.38 (1H, dd, J=5.14, 5.88), 3.50 (2H, m), 3.60 (1H, d, J=5.87), 3.74 (1H, dd, J=11.74, 2.93) 4.48 (1H, d, J=5.14), 5.81 (1H, d, J=8.07), 6.72 (1H, d, J=8.07), 9.31 (1H, s)
(4) Chemical shift by $^{13}$C-NMR: $\delta$21.4, 21.4, 23.8, 26.3, 26.8, 27.5, 28.8, 33.2, 36.3, 38.2, 47.9, 49.1, 63.6, 69.3, 71.5, 73.2, 83.9, 104.4, 119.8, 138.5, 141.6, 145.4, 145.4, 153.9, 194.3
(5) Solubility in solvents: Soluble in chloroform, acetone, ethyl acetate and methanol. Somewhat soluble in ethanol. Not soluble in water.
(6) Base, neutral or acid?: Neutral
(7) Color and other properties: Colorless oil.

From the properties and the results of structural analyses, the first of the separated compound has been determined to be the cyathane derivative shown by Formula (1).

Analyses show that a second of the aforementioned three kinds has the following physical and chemical properties and the structure:

(1) Molecular weight: 432 ($C_{25}H_{36}O^6$)
(2) Infrared spectrum: 3421, 1691, 1616 $cm^{-1}$
(3) Chemical shift by $^1$H-NMR: $\delta$0.97 (3H, d, J=6.59), 0.98 (3H, d, J=6.23), 0.99 (3H, s), 1.02 (3H, s), 1.50 (2H, m), 1.53 (2H, m), 1.58 (2H, m), 2.28 (3H, m), 2.75 (2H, m), 3.20 (1H, dd, J=8.42, 8.79), 3.35 (1H, dd, J=11.72, 10.62), 3.60 (1H, dd, J=8.79, 8.79), 3.69 (1H, m), 3.82 (1H, d, J=9.71), 4.03 (1H, dd, J=11.72, 5.86), 4.58 (1H, d, J=8.42), 5.14 (1H, d, J=9.71), 6.92 (1H, br.s), 9.56 (1H, s)
(4) Chemical shift by $^{13}$C-NMR: $\delta$16.4, 21.4, 21.9, 24.4 27.1, 27.7, 28.4, 29.7, 36.4, 38.1, 41.6, 41.9, 49.4, 66.9, 70.7, 70.9, 71.1, 74.9, 79.1, 98.5, 135.9, 140.2, 142.1, 155.4, 193.4
(5) Solubility in solvents: Soluble in chloroform, acetone, ethyl acetate and methanol. Somewhat soluble in ethanol. Not soluble in water.
(6) Base, neutral or acid?: Neutral
(7) Color and other properties: Colorless oil.

From the properties and the results of structural analyses, the second of the separated compound has been determined to be the cyathane derivative shown by Formula (2) where R is CHO.

Analyses further show that the third of the aforementioned three kinds has the following physical and chemical properties and the structure:

(1) Molecular weight: 434 ($C_{25}H_{38}O_6$)
(2) infrared spectrum: 3380, 2960, 2870, 1376, 1170, 1062, 1041, 1010 $cm^{-1}$
(3) Chemical shift by $^1$H-NMR: $\delta$0.96 (3H, d, J=6.60), 0.97 (3H, d, J=6.60), 1.00 (3H, s), 1.02 (3H, s), 1.50 (2H, m), 1.52 (1H, m), 1.63 (1H, m), 1.66 (2H, m), 2.27 (2H, m), 2.32 (1H, m), 2.41 (1H, m), 2.48 (1H, m), 2.75 (1H, heptet, J=6.60), 3.31 (1H, dd, J=10.56, 10.88), 3.41 (1H, dd, J=8.58, 8.91), 3.56 (1H, dd, J=8.91, 8.58), 3.63 (1H, m), 3.89 (1H, d, J=9.74) 3.99 (1H, dd, J=10.56, 5.40), 4.00 (1H, d, J=11.88), 4.31 (1H, d, J=11.88), 4.58 (1H, d, J=8.58), 4.81 (1H, br.d, J=9.74), 6.01 (1H, br.d, J=7.26)
(4) Chemical shift by $^{13}$C-NMR: $\delta$16.5, 21.4, 21.9, 24.5 26.9, 27.8, 28.3, 28.4, 36.5, 38.1, 41.5, 42.6, 49.4, 66.0, 66.9, 69.9, 71.3, 73.3, 74.7, 79.8, 98.7, 135.7, 136.8, 139.5, 139.8
(5) Solubility in solvents: Soluble in chloroform, acetone, ethyl acetate and methanol. Somewhat soluble in ethanol. Not soluble in water.
(6) Base, neutral or acid?: Neutral
(7) Color and other properties: Colorless oil.

From the properties and the results of structural analyses, the third of the aforementioned three separated compound has been determined to be the cyathane derivative shown by Formula (2) where R is $CH_2OH$.

As will be described below more in detail, the cyathane derivatives according to the present invention have the effect of stimulating the production of NGF as well as antimicrobial effects. It is to be noted that compounds having the effect of stimulating the production of NGF are now being considered for application as therapeutic drugs for senile dementia of Alzheimer type and those with antimicrobial effects for application to food items as natural antibacterial agents.

EXAMPLES

Test No. 1:

Extraction and separation of cyathane derivatives Mycelia of Hericium erinaceum were cultured for four weeks in an SGC medium (as described above) and culture mycelia were obtained as a precipitate by centrifugal separation. These culture mycelia (110 g as wet weight) were added to one liter of 85% aqueous solution of ethanol, and the mixture was homogenized. After it was left quietly for a day and a night at room temperature, an extract solution was obtained by filtration. A second extract solution was obtained by adding one liter of 85% aqueous solution of ethanol to the residue and processing similarly. The second extract solution thus obtained was then mixed together with the first extract solution. This combined extract solution was heated at 40°–45° C. under a reduced pressure condition to evaporate the ethanol to obtain a water phase.

To this water phase was added one liter of ethyl acetate and, after the mixture was shaken and then left quietly, the layer of ethyl acetate was separated. To the residue was added one liter of ethyl acetate, and another ethyl acetate layer was separated similarly by liquid-liquid partition extraction and mixed together with the earlier separated ethyl acetate layer. The combination was heated at 40°–45° C. under a reduced pressure condition to evaporate the ethyl acetate. It was further dried by means of a desiccator to obtain 2.1 g of a dried solid object.

The solid object thus obtained was dissolved in hexane for use in silicagel column chromatography (carrier: Wakogel C-200, trade name of Wako Pure Chemical Industries, Inc.) Use as mobile phase was made of a total of four parts of 60 ml each with volume ratios of chloroform/acetone=9/1, 8/2, 7/3 and 1/1 such that the polarity changes monotonically from one part to the next. A total of 24 parts with 10 ml each was thus obtained.

Of these 24 parts, the elution parts with volume ratio of chloroform/acetone=9/1 were added together for the same silicagel column chromatography. Use as mobile phase in this case was made of 80 ml of mixture with volume ratio of chloroform/acetone=7/3 to obtain a total of 8 parts of 10 ml each. Of these 8 parts, 73.8 mg of the cyathane shown by Formula (1) was separated from the fourth and fifth parts. From the second part, 31.9 mg of the cyathane shown by Formula (2) with R=CHO was separated.

Test No. 2:

Extraction and separation of cyathane derivatives

Mycelia of Hericium erinaceum were cultured for four weeks in an SGC medium (as described above) and culture mycelia were obtained as a precipitate by centrifugal separation. These culture mycelia (700 g as wet weight) were added to 5 liters of 85% aqueous solution of ethanol, and the mixture was homogenized. After it was left quietly for a day and a night at room temperature, an extract solution was obtained by filtration. A second extract solution was obtained by adding 5 liters of 85% aqueous solution of ethanol to the residue and processing similarly. The second extract solution thus obtained was then mixed together with the first extract solution. This combined extract solution was heated at 40°–45° C. under a reduced pressure condition to evaporate the ethanol to obtain a water phase.

To this water phase was added one liter of ethyl acetate and, after the mixture was shaken and then left quietly, the layer of ethyl acetate was separated. To the residue was added one liter of ethyl acetate, and another ethyl acetate layer was separated similarly by liquid-liquid partition extraction. This process was repeated once more, and the ethyl acetate layers obtained in the second and third processes were mixed together with the earlier separated ethyl acetate layer. The combination was heated at 40°–45° C. under a reduced pressure condition to evaporate the ethyl acetate. It was further dried by means of a desiccator to obtain 7.0 g of a dried solid object.

The solid object thus obtained was dissolved in hexane for use in silicagel column chromatography (as described above). Use as mobile phase was made of a total of four parts of 200 ml each with volume ratios of chloroform/acetone=9/1, 8/2, 7/3 and 1/1 such that the polarity changes monotonically from one part to the next. A total of 16 parts with 50 ml each was thus obtained.

Of these 16 parts, the elution parts with volume ratio of chloroform/acetone=1/1 were added together for the same silicagel column chromatography. Use as mobile phase in this case was made of 80 ml of mixture with volume ratio of chloroform/acetone=9/1 to obtain a total of 8 parts of 10 ml each. From the second of these 8 parts, 44.6 mg of the cyathane shown by Formula (2) with R=CHO was separated.

Test No. 3:

Effects of stimulating production of NGF

According to the method by Furukawa, et al., published in the Biochemical and Biophysical Research Communications, 136, 57–63 (1986), primary astroglial cells from the brain of a 19-day old rat were cultured in Dulbecco's modified Eagle's minimum essential medium (DMEM) containing 10% fetal calf serum. This was done over a period of 1–2 weeks by exchanging media once every three days. After confluence was reached, the medium was changed to DMEM containing 0.5% bovine serum albumin, and the culture process was further continued for a few days to obtain a culture base. Separately, the cyathane derivatives obtained in Test Nos. 1 and 2 were dissolved in dimethyl sulfoxide and these solutions were added to the DMEM containing 0.5% bovine serum albumin. They were then applied to the aforementioned culture base to prepare a total of 3 test parts of dosage groups such that the cyathane derivative concentration of each dosage group was 1 mM. For comparison, a sample was also prepared with only dimethyl sulfoxide, without any cyathane derivative dissolved therein, added to DMEM containing 0.5% bovine serum albumin. This comparison sample was applied to the aforementioned culture base to prepare a comparison group. After a total of three parts of test groups and one comparison group were cultured for 24 hours, culture fluids were collected and measured for the concentration of NGF by the enzyme immunoassay method of Furukawa, et al. reported in the Journal of Neurochemistry, 40, 734–744 (1983). A t-statistical test was carried out between the comparison group cultured without any cyathane derivative and each test group cultured with 1 mM of cyathane derivative applied to it. It was concluded as a result that each test sample was effective with level of significance of 1%.

Test No. 4:

Antimicrobial effects of the cyathane derivatives

An agar medium with pH=7.2–7.4, containing bouillon 1.0%, polypoptone 0.5%, sodium chloride 10.25% and agar 1.5%, was prepared, and 15 ml and 6 ml thereof were each placed in a test tube and partially sterilized inside an autoclave for 20 minutes at 121° C. by high-pressure steam. A 15 ml medium, thus partially sterilized, was poured in a sterilized manner into a partially sterilized Petri dish so as to have a flat surface serving as a base layer. Separately, a partially sterilized (by high-pressure steam) medium of 6 ml was melted, cooled to 55°–60° C., and inoculated with 50 $\mu$l of bacteria (bacillus subtilis) which had been cultured by shaking for 16 hours at 30° C. inside 5 ml of a liquid medium. After this was mixed well, it was poured as bacterial layer on top of the aforementioned base layer to serve as a test medium. Paper disks, into which a 10 mg/ml solution of each of the cyathane derivatives isolated in Test Nos. 1 and 2 was absorbed and dried, were carefully placed on top of this test medium by means of a tweezer. After 24 hours of culturing inside a thermostatic chamber of 30° C., the diameter of the generated inhibition circle was measured and the antibacterial activity (in mm) was obtained as (the measured diameter of the inhibition circle in mm)—(diameter of the paper disk=8 mm).

The antibacterial activity of the cyathane derivative shown by Formula (1) was 3 mm, that of the cyathane derivative shown by Formula (2) where R is CHO was 10 mm and that of the cyathane derivative shown by Formula (2) where R is $CH_2OH$ was 3 mm, indicating that the three types of isolated cyathane derivative according to the present invention all have an antibacterial effect against bacteria (bacillus subtilis).

Additionally, antibacterial activities of the cyathane derivative shown by Formula (2) where R is CHO were also measured in similar manners against yeast (saccharomyces cerevisiae) and fungus (aspergillus niger). The antibacterial activity was 2 mm against the yeast (saccharomyces cerevisiae) and 4 mm against the fungus (aspergillus niger), indicating that the cyathane derivatives of the present invention have antibacterial effects also against yeast (saccharomyces cerevisiae) and fungus (aspergillus niger).

In summary, the cyathane derivatives according to the present invention are effective both as a production stimulator for nerve growth factor and as an antibacterial agent.

What is claimed is:

1. A compound of the formula:

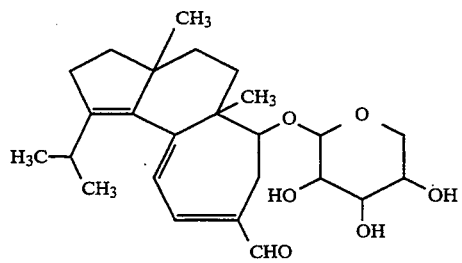

2. A compound of the formula:

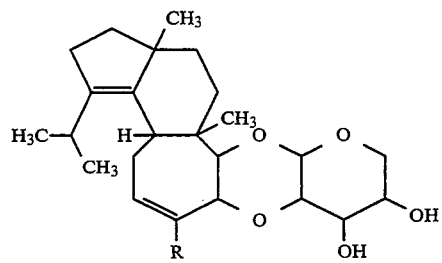

where R is either CHO or $CH_2OH$.

3. An antimicrobial composition comprising an antimicrobially effective amount of of claim 1 and a suitable carrier therefor.

4. An antimicrobial composition comprising an antimicrobially effective amount of the compound of claim 2 and a suitable carrier therefor.

* * * * *

UNITED STATES PATENT AND TRADEMARK OFFICE
CERTIFICATE OF CORRECTION

PATENT NO. : 5,391,544
DATED : February 21, 1995
INVENTOR(S) : Hirokazu Kawagishi It is certified that error appears in the above-indentified patent and that said Letters Patent is hereby corrected as shown below:

| Col. | Line | |
|---|---|---|
| 2 | 29 | /Page 4, line 6, change "chloride" to --hydrochloride--. |
| 3 | 21 | /Page 6, line 9, change "by $_1^H$-NMR:$\delta$ 0.91" to --by $^1$H-NMR: $\delta$ 0.91--. |
| 3 | 30 | /Page 6, line 17, change "by $^{12}$C-NMR:$\delta$ 21.4," to --by $^{13}$C-NMR: $\delta$ 21.4,--. |
| 3 | 48 | /Page 7, line 9, change "by $^1$H-NMR:$\delta$0.97" to --by $^1$H-NMR: $\delta$ 0.97--. |
| 3 | 56 | /Page 7, line 16, change "by $^{12}$C-NMR:$\delta$16.4," to --by $^{13}$C-NMR: $\delta$ 16.4,--. |
| 4 | 7 | / Page 8, line 10, change "by $^1$H-NMR:$\delta$0.96" to --by $^1$H-NMR: $\delta$ 0.96--. |
| 4 | 18 | / Page 8, line 19, change "by $^{12}$C-NMR:$\delta$16.5," to --by $^{13}$C-NMR: $\delta$ 16.5,--. |

Signed and Sealed this

Thirteenth Day of February, 1996

Attest:

BRUCE LEHMAN

Attesting Officer

Commissioner of Patents and Trademarks